United States Patent
Drews et al.

(10) Patent No.: US 8,579,628 B2
(45) Date of Patent: Nov. 12, 2013

(54) ARRANGEMENT COMPRISING AN INSTRUMENT FOR THE PREPARATION OR EXECUTION OF THE INSERTION OF AN IMPLANT

(75) Inventors: Dirkjoachim Drews, Plankstadt (DE); Frank Obermeier, Heppenheim (DE); Dietrich Wolf, Oberkochen (DE)

(73) Assignee: Friadent GmbH, Mannheim (DE)

( * ) Notice: Subject to any disclaimer, the term of this patent is extended or adjusted under 35 U.S.C. 154(b) by 448 days.

(21) Appl. No.: 12/448,835

(22) PCT Filed: Jan. 8, 2008

(86) PCT No.: PCT/EP2008/000067
§ 371 (c)(1),
(2), (4) Date: Sep. 22, 2009

(87) PCT Pub. No.: WO2008/089885
PCT Pub. Date: Jul. 31, 2008

(65) Prior Publication Data
US 2010/0062389 A1      Mar. 11, 2010

(30) Foreign Application Priority Data
Jan. 26, 2007   (DE) .......................... 10 2007 004 948

(51) Int. Cl.
*A61C 3/00* (2006.01)
(52) U.S. Cl.
USPC .......................................................... 433/75
(58) Field of Classification Search
USPC .............. 433/72–76, 172–176; 76/5.1, 108.1
See application file for complete search history.

(56) References Cited

U.S. PATENT DOCUMENTS

| | | | |
|---|---|---|---|
| 4,998,881 A * | 3/1991 | Lauks | 433/173 |
| 5,320,529 A | 6/1994 | Pompa | |
| 5,746,551 A * | 5/1998 | Skaggs | 408/1 R |
| 5,888,034 A | 3/1999 | Greenberg | |
| 5,967,777 A | 10/1999 | Klein et al. | |
| 7,141,074 B2 * | 11/2006 | Fanger et al. | 606/80 |
| 2005/0170311 A1 | 8/2005 | Tardieu et al. | |
| 2006/0260110 A1 | 11/2006 | Klann | |
| 2010/0297574 A1 * | 11/2010 | Llop et al. | 433/75 |
| 2010/0311006 A1 * | 12/2010 | Lancieux et al. | 433/75 |

FOREIGN PATENT DOCUMENTS

| | | |
|---|---|---|
| DE | 2205 314 | 8/1973 |
| EP | 1 207 792 | 6/2005 |
| EP | 1 447 055 | 6/2006 |
| WO | WO-02/100290 | 12/2002 |

* cited by examiner

*Primary Examiner* — Cris L Rodriguez
*Assistant Examiner* — Mirayda A Aponte
(74) *Attorney, Agent, or Firm* — Jordan and Hamburg LLP (57) ABSTRACT

An arrangement including an instrument for the insertion of a dental implant including a template placeable on a bone or surrounding tissue. The template, or a first sleeve arranged within the template, includes a through-recess, through which the instrument can be guided. The arrangement enables exact alignment and guidance of the instrument and easy handling. A second sleeve that is axially displaceable on the instrument is provided, and axially fixed in a base position through automatically releasable connecting elements with predetermined retaining force such that when the retaining force is exceeded, the connecting elements can be automatically released and the second sleeve can be axially displaced. The instrument, together with the axially fixed second sleeve, can be inserted in the continuous recess and is aligned in the template via the outer surface of the second sleeve, the surface being configured relative to the inner surface of the recess.

14 Claims, 5 Drawing Sheets

ARRANGEMENT COMPRISING AN INSTRUMENT FOR THE PREPARATION OR EXECUTION OF THE INSERTION OF AN IMPLANT

BACKGROUND OF THE INVENTION

The invention relates to an arrangement for preparing or executing the insertion of an implant, in particular a dental implant.

Such an arrangement is known from U.S. Pat. No. 5,320, 529 and includes an instrument embodied as a drill and a template by means of which the positioning and insertion of a bore in a bone, in particular the jaw bone, can be determined. The template, which may also be called a splint or is embodied as such or rail, is produced based on data about the bone, in particular the jaw bone, that are generated by means of a computer tomograph (CT), an X-ray device, or another image-producing device in order to be able to plan and define the required position of the implant, taking into account the anatomical, surgical, and also esthetic considerations. The rail is adapted to the individual situation and qualities and includes at least one through-recess for receiving a first sleeve. This first sleeve includes a through-hole through which the instrument embodied as a drill can be passed in order to be able to determine exact positioning or orientation of the bore for the implant. The inner diameter of the through-hole for the aforesaid sleeve is matched to the outer diameter of the drill for adding the bore to the bone. The drill includes an annular collar or stop that can be positioned against the free upper edge of the sleeve in order to thus define the depth of the bore in the bone. In practice there are problems when inserting an implant into the bore added by means of the arrangement, which bore is also called a prepared implant bed, especially in that it is difficult for the operator to control the insertion depth for the implant.

Moreover, when the drill is inserted into the sleeve, the drill and/or the interior surface of the sleeve may be damaged, in particular as a result of an imprecise coaxial starting orientation for the drill relative to the through-hole for the sleeve. The inner diameter of the through-hole for the sleeve is at least equal in size to the outer diameter of the drill, which after being inserted into the through-hole in a slide fit can be moved and/or is rotatable therein. If the clearance or difference in diameters between the outer diameter of the drill and the inner diameter of the through-hole is too great, the precise orientation and insertion of the bore is jeopardized. Moreover, there is the risk that as soon as the contact surface of the drill moves into position against the contact surface of the sleeve and the rotation of the drill does not immediately cease, the sleeve will heat up significantly due to the friction losses that occur. Consequently, the fixed seat of the sleeve, in the template that normally comprises plastic, is no longer assured, and there is the risk that the drill will expand the bore just added to the bone and/or will change its orientation in an impermissible manner.

Furthermore, known from DE 22 05 314 C3 is an apparatus for infusing liquid means into the bones, which apparatus includes an outer tube, whose end that is to be inserted into the bone tissue has a male thread. The apparatus furthermore includes an inner tube having a pointed tip with openings for the injection and at the opposing end has a cannula. A limiter is provided on the outer sleeve and above the punctured skin can be fixed in a position, a screw being used for fastening. The limiter embodied on the sleeve only enables limiting the apparatus insertion depth into the bone.

SUMMARY OF THE INVENTION

Proceeding from this point, the underlying object of the invention is to avoid the aforesaid problems and to refine the arrangement such that exact orientation and/or guidance of the instrument, and/or handling when work is being performed with the instrument and/or during insertion of the implant into the prepared implant bed or in particular when the mucous membrane is being punched and/or when the bore is being made in the bone, are attained with great reliability. The arrangement should have a simple structure and in particular the template should be used in combination with different instruments such as punch, drill, thread cutter, and screwing-in tool. The arrangement should have a simple and also functionally reliable structure and/or sound, reliable handling when performing processing steps by means of the instrument.

The inventive arrangement is distinguished by a simple structure that is appropriate to its function and in a simple manner and with no problem makes it possible to precisely orient and/or guide and/or position the instrument relative to the bone and/or the mucous membrane present outside on the bone. The instrument can be embodied for different work processes, especially those that involve a punch for preparing the mucous membrane in the area of the implant to be inserted, a drill, a thread cutter for creating a female thread in the implant bed, and furthermore a screwing-in tool. The following explanations, structural features, advantages, and mechanical relationships when embodying the instrument as a drill also apply analogously for instruments embodied in a different manner. It is furthermore established that in the framework of the invention the recess or through-hole provided for the instrument to pass through can be present either directly in the template or indirectly in a first sleeve that is integrated in the template, the recess in the first sleeve also being called a through-hole. Arranged on the instrument is a second sleeve, the outer contour of which is matched to the inner contour of the through-hole, in particular of the first sleeve connected to the template. The instrument is not guided directly in the through-hole of the first sleeve or template, but rather indirectly by means of the second sleeve or sliding sleeve. When the second sleeve is in the basic position, the tip of the instrument preferably projects out of the second sleeve by a pre-determined length, and the instrument thus can initially be inserted into the aforesaid through-hole, even not precisely coaxially, specifically until the end of the second sleeve that faces the tip of the instrument engages in the through-hole. The second sleeve is fixed axially in a basic position on and/or relative to the instrument by means of releasable retaining elements and/or locking elements such that after a pre-specified axial retention force is exceeded the second sleeve is automatically displaceable axially on the instrument, specifically in particular axially away from the free end of the instrument, which then can be inserted into the mucous membrane surrounding the bone and/or into the bone. The retaining and/or locking elements are arranged on the instrument, preferably in an area outside of processing surfaces, such as cutting surfaces of a drill or the like, such processing surfaces being disposed between the tip or the free end of the instrument and the area having the retaining and/or locking element. After the automatic disengagement and/or release of the retaining and/or locking elements of the instrument and the second sleeve, which shall hereinafter also be referred to as a guide sleeve, the latter is axially displaceable on the instrument, in particular to a pre-specified stop. The shaft of the instrument is preferably embodied cylindrical and/or smooth and/or as a guide surface for the sliding sleeve and/or its interior surface, for the purpose of reliably guiding the sliding sleeve after its automatic disengagement, between the area in which the sliding sleeve is disposed in the basic position and the stop. The outer contour of the second sleeve is advantageously embodied essentially cylindrical and/or unthreaded, and thus smooth, as is the interior surface of the through-hole and/or of the first sleeve.

Advantageously the interior surface of the first sleeve and the associated exterior surface of the second sleeve have smooth and/or polished surface structures. The inner diameter of the through-hole and/or of the first sleeve is significantly larger than the outer diameter of the instrument that is guided in the second sleeve. The difference in diameter between the interior surface of the first sleeve and the outer diameter of the instrument is essentially equal to twice the wall thickness of the second sleeve. When the instrument is placed into the through-hole of the template or of the first sleeve, due to the aforesaid difference in diameter the risk of damage to the first sleeve is largely precluded. The second sleeve is fixed on the instrument by means of releasable connecting elements. The automatic and/or self-actuating releasable connection is arranged and/or embodied such that when a pre-specified axial force is attained the connection is automatically released and the guide sleeve is then axially displaceable on the instrument. The retaining elements are preferably embodied as locking elements that correspond to one another and are engaged with one another but that also release automatically when the pre-specified retaining force is attained. Moreover, the instrument and the sleeve or guide sleeve are matched to one another such that after the release and/or disengagement of the connection the instrument is guided axially in and/or by means of the sleeve and thus precise handling of the instrument is attained, for instance during further or deeper insertion of a drill into the bone. The instrument is guided precisely, the second sleeve being arrested axially and/or radially with respect to the template, in particular by stops that have been matched to one another, with respect to the template. The second sleeve or displaceable sleeve has a contact surface that is associated with a stop surface of the template or of the first sleeve such that the connecting elements are automatically released or disengaged when the aforesaid surfaces are positioned against them and the aforesaid axial force is effective.

The second sleeve is advantageously releasably fixed on the instrument such that before the tip of the instrument reaches the bone the second sleeve is already at least partially inserted into the first sleeve and thus the instrument, for instance the drill, is already reliably oriented with respect to the bone when the drilling of the latter begins. As drilling continues, the second sleeve then moves until its stop is positioned against an associated stop for the first sleeve so that after an axial force has continued its action in the longitudinal direction to the drill bit, the releasable connection of the second sleeve on the drill is automatically disengaged and the drill can now be moved through the second sleeve for further drilling of the bone. Thus functionally reliable and/or axis-parallel and/or coaxial guidance of the instrument is assured. Adding the bore ends as soon as a stop on the drill is positioned against the first sleeve fixed in the template indirectly via the second sleeve, this furthermore defining the insertion depth. It is herein expressly stated that these explanations also apply analogously when a different instrument is used, for instance a punch for the mucous membrane or a thread cutter or a screwing-in tool for the implant. The proposed arrangement is inventively used during the preparation or execution of the insertion of an implant and is furthermore embodied in accordance with the invention for executing a method for preparing or inserting an implant.

Refinements and special embodiments of the invention are provided in the subordinate claims and the following description.

The invention shall be explained in greater detail in the following using the special exemplary embodiments depicted in the drawings, but this shall not constitute a limitation.

DETAILED DESCRIPTION OF THE INVENTION

Figure 1:
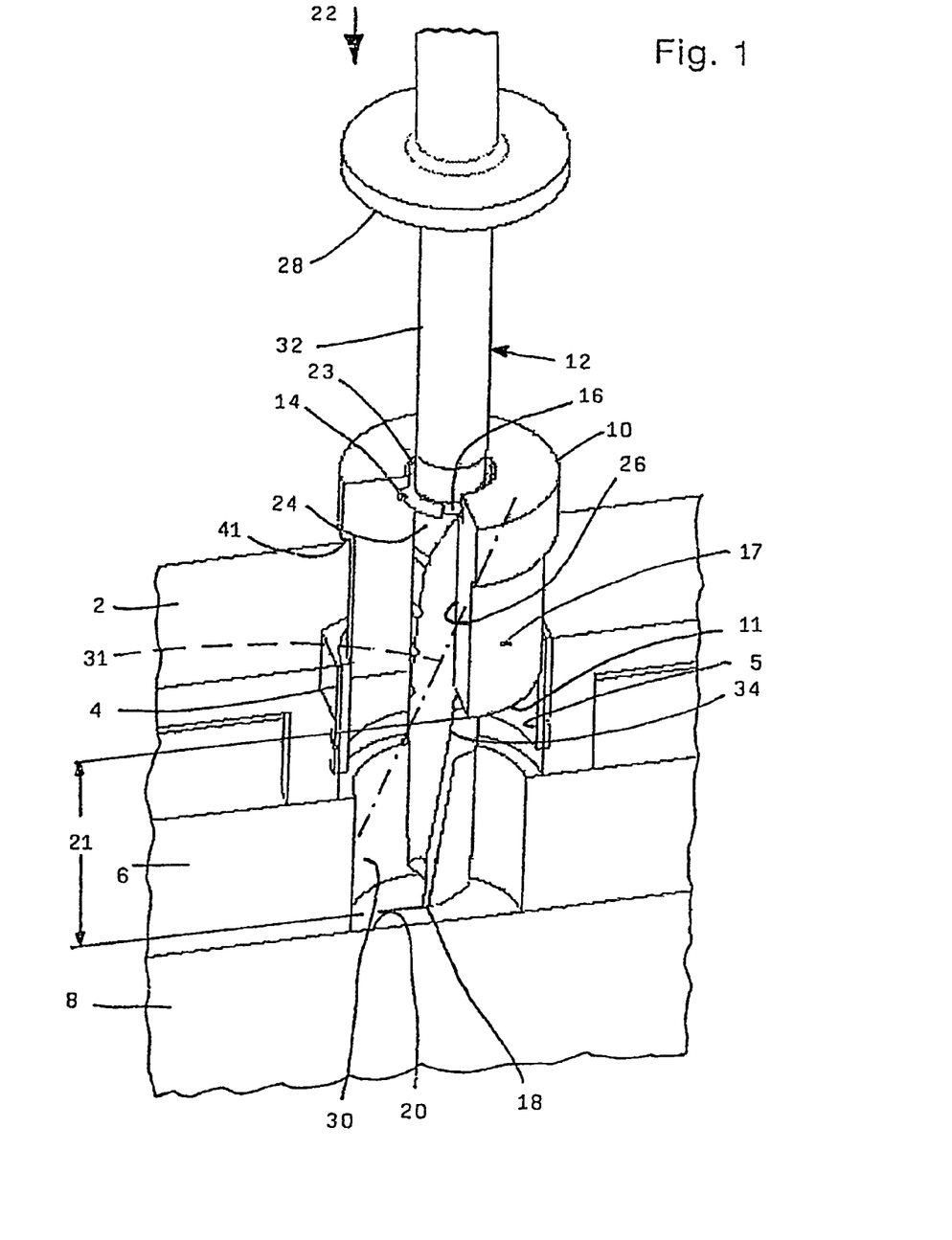
FIG. 1 is a perspective partial cut-away depiction of the arrangement, the instrument being embodied as a drill.

In accordance with FIG. 1, the inventive arrangement includes a template 2 in which a first sleeve 4 is arranged and secured against rotation in particular due to a non-round exterior surface. The template 2 and/or the first sleeve 4 contain a through-recess 5. The template 2 with the preferably integrated first sleeve 4 is placed on a mucous membrane or mucosa 6 that is disposed over a bone 8, in particular a jaw bone. The lower end 11 of a second sleeve 10 that is arranged on an instrument in the form of a drill 12 is already partially inserted into the first sleeve 4 or the recess 5. The second sleeve 10 is fixed on the instrument or drill 12 by means of automatically releasable connecting elements 14, 16. The connecting elements 14, 16 are inventively embodied as locking elements that are matched to one another and/or that engage in one another and that disengage when a pre-specified axial force is exceeded so that the sleeve 10 subsequently is axially displaced on the instrument, which here is embodied as a drill 12. The second sleeve 10 has an exterior surface 17 that is matched and/or adapted to the interior surface of the recess 5. The exterior surface 17 and the aforesaid interior surface of the recess 5 are preferably embodied cylindrically such that the second sleeve 10 is rotatable and/or axially displaceable in the recess 5 with essentially no clearance.

For the sake of simplicity, in the following the instrument shall be called a drill 12; however, in the framework of the invention the instrument can also be embodied as a punch, thread cutter, or screw-in tool for the implant. The second sleeve 10 is fixed on the drill 12 in a preferred manner such that the second sleeve 10, as depicted, is at least partially inserted into the first sleeve 4 or the recess 5 before the drill bit 18 reaches the surface 20 of the bone 8. The bit 18 projects beyond the lower end 11 of the second sleeve or sliding sleeve 10 in its base position by the length 21. The first releasable connecting element 14 is advantageously embodied as an elastic ring and/or an expandable spring element and is partly arranged in an annular groove in the interior surface of the second sleeve 10. In its exterior surface, the drill 12 includes the second releasable connecting element 16, which here is embodied as an annular groove in which engages the correspondingly embodied first connecting element 14 of the second sleeve 10. The connecting elements 14, 16 that correspond to one another are embodied such that when a pre-specifiable axial force in accordance with arrow 22 is exceeded, the releasable connection that the elements 14, 16 enable between drill 12 and second sleeve 10 is disengaged. As can be seen, the second sleeve 10 includes a through-hole 23 through which the drill 12 passes. The drill 12, or its exterior surface 24, is matched to the second sleeve 10, or its interior surface 26, such that the second sleeve 10 is displaceable on the drill 12 after the automatic disengagement of the releasable connecting elements 14, 16. The second sleeve 10 can thus also be called a sliding sleeve that is axially displaceable in the axial direction on the exterior surface of the drill, the drill 12 furthermore being rotatably arranged in the sliding sleeve 10. It is expressly noted that the drill 12 can preferably also be rotated in the sliding sleeve 10 when the releasable connecting elements 14, 16 between the sliding sleeve 10 and the drill 12 have not been disengaged. The sliding sleeve 10 is axially fixed on the drill 12 by means of the releasable connecting elements 14, 16, the rotation of the drill 12 also be enabled in the sliding sleeve 10. The drill 12 furthermore includes a stop 28 that is embodied here as an annular collar. In the depicted basic position of the sliding sleeve 10, which position is assured by means of the connecting elements 14, 16 there is a pre-specified axial distance between the sliding sleeve 10 and the stop 28, and this distance defines the insertion depth into the bone 8 for the drill 12 or drill bit 18.

Prior to introducing the drill with the sliding sleeve 10 into the template 2, an opening 30 was made in the mucous membrane or mucosa 6 by means of an appropriate instrument, for instance a punch tool. The aforesaid punch tool is also embodied and/or adapted to the template 2 and/or its first sleeve 4 such that there is reliable orientation and guidance. The aforesaid punch tool is also a component of the inventive arrangement. It should also be noted that, as indicated by the dot-dash line 31, the tip 18 of the drill or instrument 12 can initially be engagingly inserted into the first sleeve 4 at an angle until the end 11 of the sliding sleeve 10 is caused to engage with the first sleeve 4 and thus the coaxial orientation of the instrument 12 with the through-hole is achieved.

Additionally or alternatively, instead of a closed annular embodiment, the sliding sleeve 10 can have an axial slit such that the sliding sleeve 10 can be laterally moved on and/or clipped to the drill 12. In this case the sliding sleeve 10 comprises an advantageously resiliently elastic material, especially plastic. Such an embodiment essentially corresponds to the embodiment of the sliding sleeve 10 depicted in cut-away in FIG. 1.

Moreover, the sliding sleeve 10 can be fixed on the essentially cylindrical drill shaft 32 or in the cutting area 34 or on the drill chuck (not depicted here), the stop 28 naturally being arranged at a different location in the latter case. Furthermore, in the framework of the invention the stop can be embodied as a component of the drill chuck or can be embodied using a corresponding element of the drill device. Regardless of the specific configuration of the releasable connecting elements 14, 16 and their spatial arrangement on and/or at the drill and/or their spatial relationship to the drill, what is determinant is that the sliding sleeve 10 is initially fixed or when it is delivered from the plant is fixed or in the basic position is fixed axially in a defined manner on the drill by means of releasable connecting elements and that furthermore after the release or disengagement of the connecting elements a defined axial guidance and/or displacement is made possible that is limited by the stop 28 after a pre-specified displacement path has been traveled.

Figure 2:
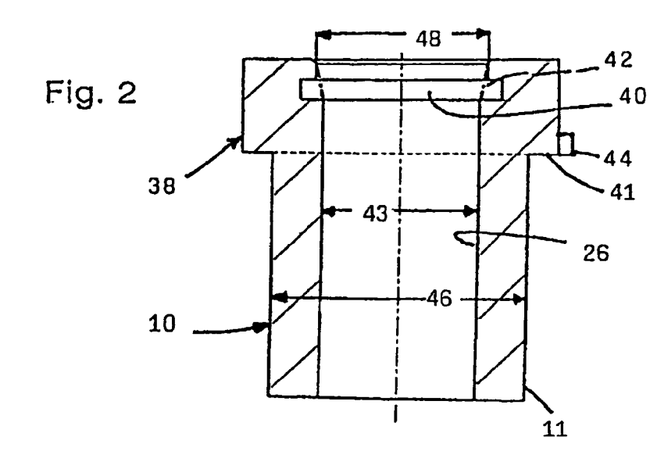
FIG. 2 depicts a section of the second displaceable sleeve in an axial plane.

FIG. 2 depicts a section through the sliding sleeve 10, which includes in its interior surface 26, preferably its upper end area 38, an annular groove 40 for receiving some of the first releasable connecting element. The lower end surface 41 of the end area 38 embodied as an annular collar with an expanded diameter, the end surface 41 that faces the tip of the instrument, forms the contact surface of the sliding sleeve 10 on the template and/or of the first sleeve integrated therein. If the lower end surface 41 comes to be positioned against the template and/or the integrated first sleeve and if the axial advancing force continues to be in effect, the connection between the sliding sleeve 10 and the drill or instrument is automatically released and/or released without any additional measures. As the dot-dash line 42 indicates, in the framework of the invention the first releasable connecting element can furthermore be embodied as a conical element, or can include such an element, that cooperates with a correspondingly embodied element of the instrument, especially the drill, this also advantageously providing security against rotation. The cone angle or angles are pre-specified such that there is no conical self-locking, but rather there is the releasable connection. Proceeding from the annular groove 40 to the lower end 11, the sliding sleeve 10 or its interior surface 26 possesses a uniform inner diameter 43. It is established that the inventive arrangement includes various sliding sleeves 10, specifically with different sized inner diameters 43 that are matched to different sized outer diameters of various drills and instruments. Furthermore, in such sliding sleeves the inner diameter of the annular grooves 40 and of the connecting elements arranged therein are correspondingly embodied and/or matched.

Furthermore, provided outside on the sliding sleeve 10 is a stop element 44 with which an additional stop element of the first sleeve and/or of the template corresponds such that, as soon as they engaged with one another and/or are positioned against one another, the initially specified rotation is stopped and the sliding sleeve is secured against rotation with respect to the template and/or the first sleeve. Apart from the upper, expanded end area 38, the sliding sleeve 10 has an outer diameter 46 that is matched to the inner diameter of the first sleeve, and specifically advantageously such that there is a slide fit and/or such that after engaging in the first sleeve the sliding sleeve 10 slides in and out of it easily and/or with no clearance, specifically both axially and rotatably. It is expressly stated that the sliding sleeves with different inner diameters 43 each have the same outer diameter 46. Above the annular groove 40 for the connecting element the sliding sleeve 10 has an inner diameter 48 that is preferably specified larger than the inner diameter 43 of the interior surface 26 connecting from the annular groove 40 to the lower end 11. Thus it is assured in a preferred manner that during and/or after the release of the connection to the instrument the connecting element arranged in the annular groove 40 is not pressed downward into the area of the interior surface 26, but rather can be partly drawn and/or moved upward into the area with the expanded diameter 48. As can be seen, the inner diameter of the annular groove 40 is provided larger than the inner diameter 48 of the adjacent area thereabove.

Figure 3:
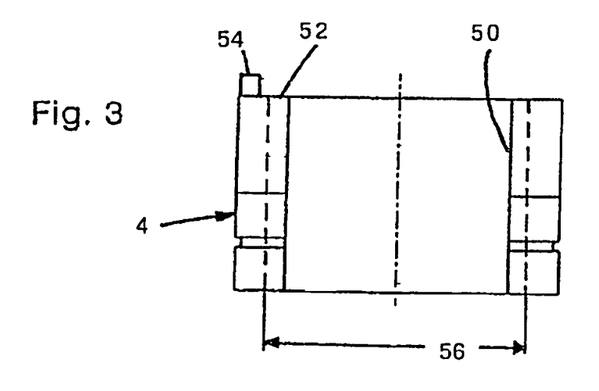
FIGS. 3, 4 depict the first sleeve in an axial section and in a perspective elevation.
Figure 4:
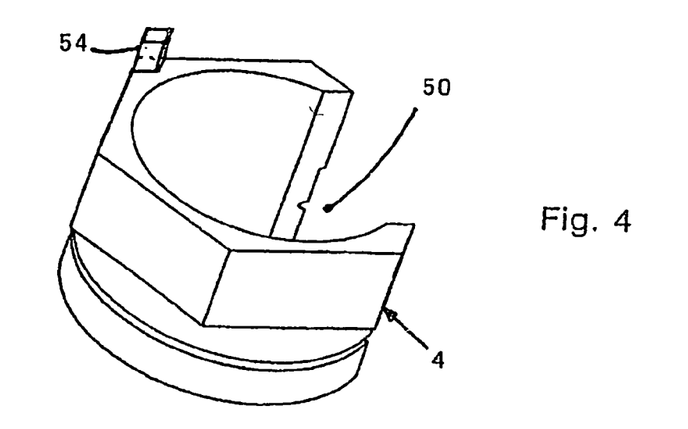

FIGS. 3 and 4 provide lateral and perspective elevations, respectively, of the first sleeve 4. The first sleeve 4 includes a lateral slit 50 that extends at least part of the way down from the upper end face 52, preferably across the entire axial length, in accordance with the drawing. The first sleeve 4 has an at least partly non-round exterior contour, for instance in the shape of a polygon, so that it can be integrated into the template rotation-fast. Moreover, the template also includes a recess or a slit corresponding to the lateral slit 50 of the sleeve 4 such that the instrument or its tip can be inserted laterally, where necessary on an incline, into the template and/or the first sleeve. Thus, corresponding to the axial length of the slit of the first sleeve 4 and/or of the template, the space requirement is minimized and handling when inserting the instrument is simple, even in constrained spaces, such as for instance oral cavity. Preferably provided in the area of the upper end face 52 is the aforementioned additional stop 54 with which the stop element for the sliding sleeve can be caused to engage or against which it can be positioned. The first sleeve 4 includes interiorly a through-hole having an inner diameter 56 that is matched to the outer diameter of the sliding sleeve and is at least essentially the same size in order to assure certain guidance of the sliding sleeve in the first sleeve. It is stated at this point that in the framework of the invention the first sleeve can be omitted and the instrument can be guided directly in a recess of the template, the configuration of the interior surface of this recess corresponding to the interior surface of the first sleeve.

Figure 5:
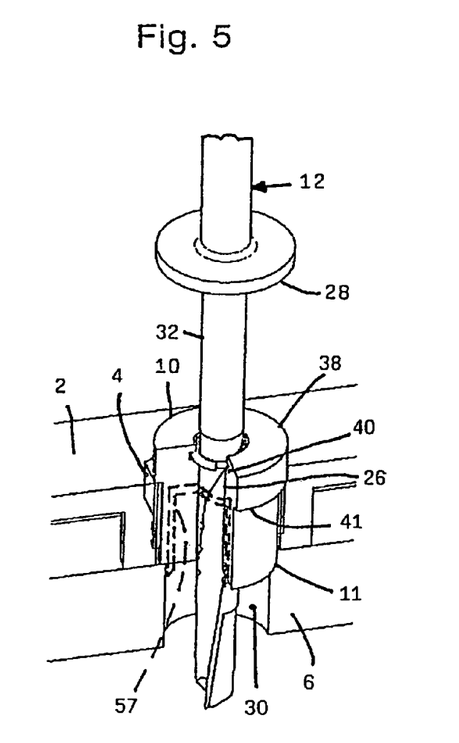
FIGS. 5, 6 depict the arrangement with the drill in different positions while the bore is being added to the bone.
Figure 6:
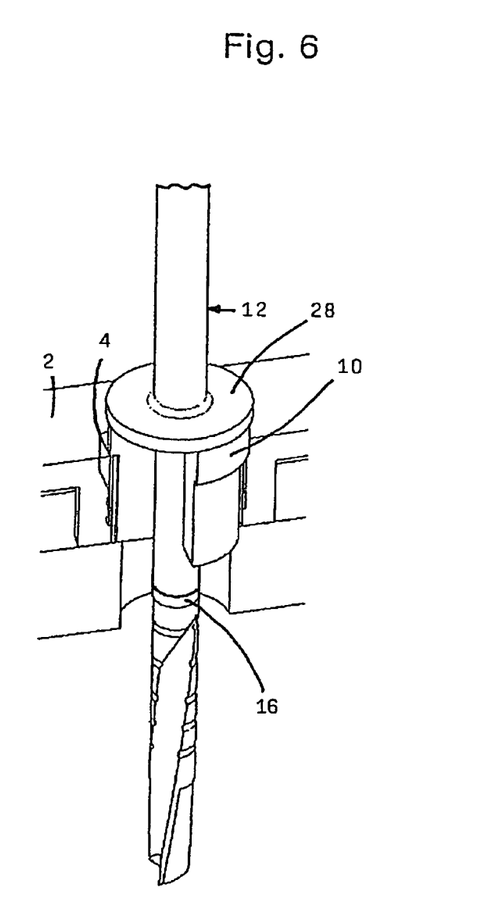

FIGS. 5 and 6 depict additional phases of the insertion of the instrument or drill, the bone not being displayed as it is in FIG. 1. In accordance with FIG. 5, the drill 12 has been moved toward the template 2 and/or the first sleeve 4 such that the lower end surface 41 of the expanded upper edge area 38 of the sliding sleeve 10 is positioned against the template 2 and/or the first sleeve 4. If there is further axial movement by the drill 12, and simultaneous rotational movement thereof, further rotation of the sliding sleeve is prevented by means of the two stop elements that are positioned against one another or engaged with one another, while the rotation of the drill 12 can continue unchanged. As can be seen from FIG. 6, the axial movement of the drill is terminated in that the stop or annular collar 28 of the drill 12 comes to be positioned against the upper end face of the sliding sleeve 10, which is already axially fixed with respect to the template 2 and/or the first sleeve.

One alternative embodiment of the instrument 12 as a punch is depicted by a dashed line 57 in FIG. 5. This punch 57 is arranged on the shaft 32 at a pre-specified distance beneath the annular groove 40. The punch 57 is pot-shaped and embodied open in the downward direction toward the mucous membrane 6. The connecting part of the drill according to FIG. 5 is not used here.

After the connection between the sliding sleeve 10 and the instrument 12 embodied in this manner has been released, the opening 30 is made in the mucous membrane 6 by means of the punch 57.

Figure 7:
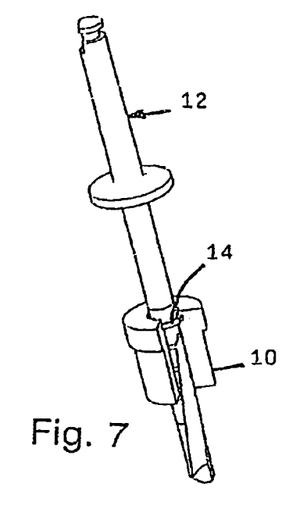
FIGS. 7, 8 depict perspective elevations of the drill with the displaceable sleeve.
Figure 8:
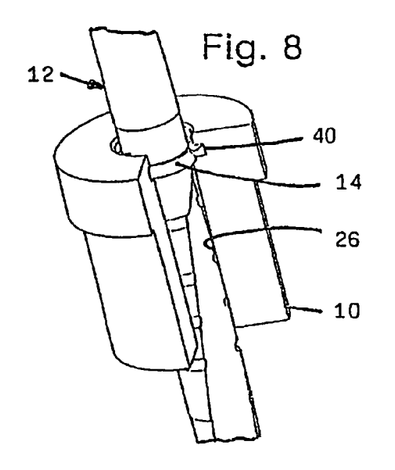

FIGS. 7 and 8 provide perspective elevations of the instrument 12 embodied as a drill together with the sliding sleeve 10. The first connecting element 14, arranged in the retaining or annular groove 40 of the sliding sleeve 10, is embodied here as a slit spring. The spring ring engages a radially interior surface area in part in the second connecting element of the drill 12, which element is embodied as an annular groove. If a pre-specified axial force of the drill 12 is exceeded with respect to the sliding sleeve 10, the spring ring is pressed out of the annular groove or the second connecting element and the connection is thus released.

Figure 9:
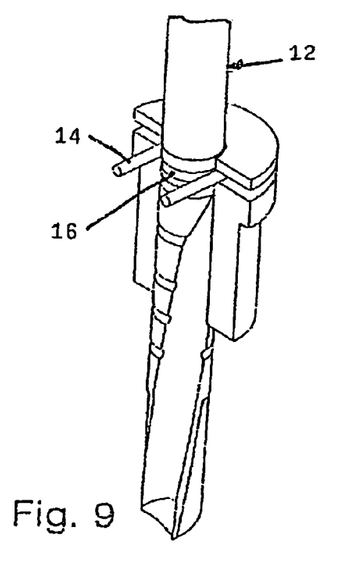
FIGS. 9, 10 depict special embodiments of the releasable connection between the second sleeve and the drill.
Figure 10:
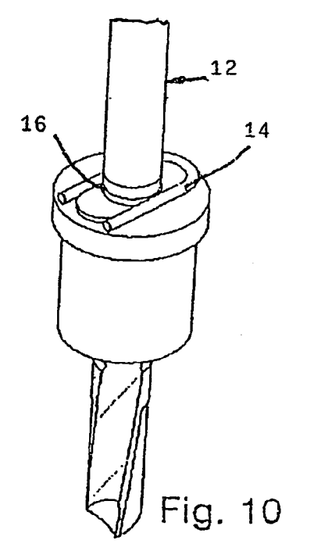

FIGS. 9 and 10 depict partial cut-away perspective elevations of additional exemplary embodiments of the releasable connection, the first connecting element 14 being embodied as a clip spring. Some of the interior surface areas of the clip spring engage in the second connection element 16 of the drill 12, which element is again embodied as an annular groove.

Figure 11:
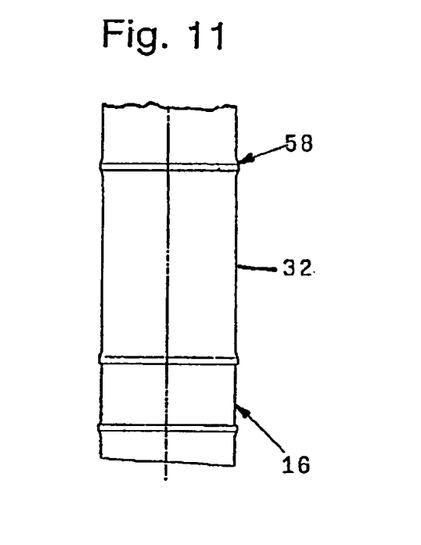
FIG. 11 depicts a first perspective elevation view of a second alternative embodiment of the releasable connection between the second sleeve and the drill.
Figure 12:
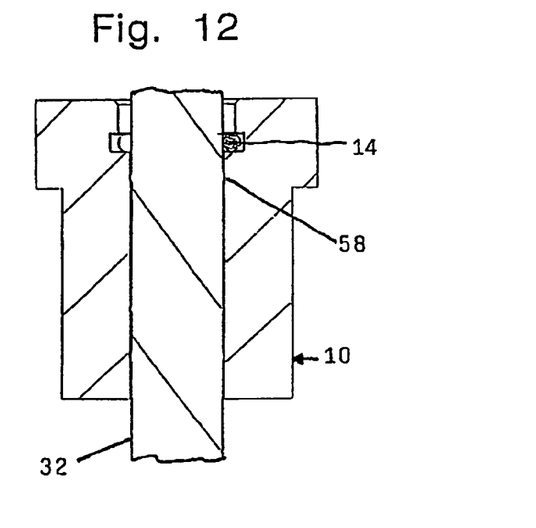
FIG. 12 depicts a second perspective elevation view of the second alternative embodiment of the releasable connection between the second sleeve and the drill.

FIGS. 11 and 12 depict another exemplary embodiment for the releasable fixation of the sliding sleeve 10, depicted on the shaft 32 of the drill. The shaft 32 includes for the sliding sleeve 10 both a usefully annular guide cam 58 and the second connecting element 16, which is embodied as a retaining groove. Since the retaining groove 16 has a longer axial longitudinal extension than the first connecting element 14 or spring element, the sliding sleeve is axially displaceable to a certain degree with respect to the drill 12, even when the connection has not been disengaged. Due to the guide cam or cams 58 it is assured that the sliding sleeve 10 moves easily on the drill 12 in a particularly useful manner.

Figure 13:
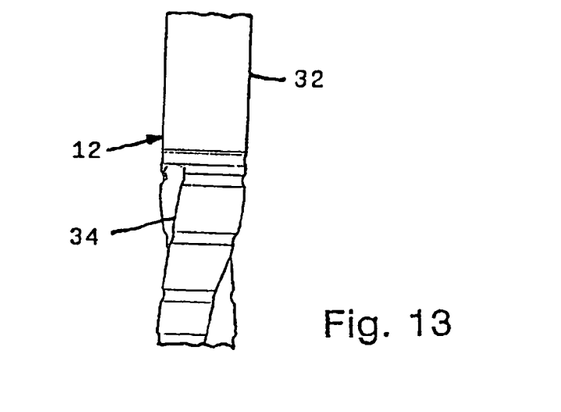
FIG. 13 is a view of a special shaft geometry.

Finally, FIG. 13 depicts a view of a specific geometry of the drill shaft 32. The second connecting element 12, which is embodied here as an annular groove, is arranged between the usefully cylindrical shaft 32 and the cutting area 34.

The invention claimed is:

1. A dental implant apparatus comprising an instrument for preparing or executing insertion of a dental implant, a template configured to be placed on a bone or tissue surrounding the bone, said template or a first sleeve arranged in said template having a through-recess configured for passage therethrough of at least part of said instrument, an axially displaceable second sleeve that in a basic position is axially fixed on the instrument with pre-specified retention force by means of automatically releasable connecting elements, at least one of said releasable connecting elements being received within another of said releasable connecting elements, and wherein when the retention force is exceeded said connecting elements are automatically releasable whereupon said second sleeve is axially displaceable on said instrument, and said instrument together with said axially fixed second sleeve being insertable into said through-recess and thereupon being guided and/or oriented in said template via the exterior surface of said second sleeve, an exterior surface of said instrument and an interior surface of said second sleeve are so dimensioned that the second sleeve is slidably fitted on the instrument with a slight or nearly zero clearance.

2. A dental implant apparatus comprising an instrument for preparing or executing insertion of a dental implant, a template configured to be placed on a bone or tissue surrounding the bone, said template or a first sleeve arranged in said template having a through-recess configured for passage therethrough of at least part of said instrument, an axially displaceable second sleeve that in a basic position is axially fixed on the instrument with pre-specified retention force by means of automatically releasable connecting elements, at least one of said releasable connecting elements being received within another of said releasable connecting elements, and wherein when the retention force is exceeded said connecting elements are automatically releasable whereupon said second sleeve is axially displaceable on said instrument, said instrument together with said axially fixed second sleeve being insertable into said through-recess and thereupon being guided and/or oriented in said template via the exterior surface of said second sleeve, an exterior surface of said instrument and an interior surface of said second sleeve are so dimensioned that the second sleeve is slidably fitted on the instrument with a slight or nearly zero clearance, said second sleeve has a contact surface positionable against said template and/or said first sleeve such that when the contact surface is urged against said template and/or said first sleeve the retention force is exceeded whereupon said connecting elements are automatically released, the basic position of the second sleeve is so predetermined that after a tip portion of said instrument has been at least partly inserted into said recess so that said guiding and orientation is effected, said automatic release occurs whereupon said second sleeve is slidable on the instrument, the apparatus further comprising stops on said second sleeve and said template or said first sleeve, said stops being located and configured to limit rotational movement of said second sleeve with respect to said template and/or said first sleeve, said connection between said second sleeve and said instrument being releasable when said limit has been attained and/or after a predetermined axial displacement of said second sleeve with respect to said template and/or said first sleeve due to application of an axial force.

3. A dental implant apparatus comprising an instrument for preparing or executing insertion of a dental implant, a template configured to be placed on a bone or tissue surrounding the bone, said template or a first sleeve arranged in said template having a through-recess configured for passage therethrough of at least part of said instrument, an axially displaceable second sleeve that in a basic position is axially fixed on the instrument with pre-specified retention force by means of automatically releasable connecting elements and wherein when the retention force is exceeded said connecting elements are automatically releasable whereupon said second sleeve is axially displaceable on said instrument, and said instrument together with said axially fixed second sleeve being insertable into said through-recess and thereupon being guided and/or oriented in said template via the exterior surface of said second sleeve, an exterior surface of said instrument and an interior surface of said second sleeve are so dimensioned that the second sleeve is slidably fitted on the instrument with a slight or nearly zero clearance, said first sleeve is integrated into said template, and the apparatus including stops arranged on said first sleeve and said second sleeve for securing said second sleeve against rotation with respect to said integrated first sleeve.

4. The dental implant apparatus in accordance with claims 1 or 3, wherein said second sleeve has a contact surface positionable against said template and/or said first sleeve such that when the contact surface is urged against said template and/or said first sleeve the retention force is exceeded whereupon said connecting elements are automatically released.

5. The dental implant apparatus in accordance with claim 4, wherein the basic position of the second sleeve is so predetermined that after a tip portion of said instrument has been at least partly inserted into said recess so that said guiding and orientation is effected, said automatic release occurs whereupon said second sleeve is slidable on the instrument.

6. The dental implant apparatus in accordance with claims 1, 2 or 3, wherein an outer diameter of said instrument is significantly smaller than an inner diameter of said first sleeve or said through-recess of said template, and said first sleeve is integrated in said template, or said first sleeve is secured against rotation in said template.

7. The dental implant apparatus in accordance with claim 6, wherein said second sleeve is insertable with axial guidance into said through-recess to a predetermined depth.

8. The dental implant apparatus in accordance with claims 1, 2 or 3, wherein an exterior surface of said second sleeve and an interior surface of said through-recess are so dimensioned that the second sleeve is slidable in the through-recess with a slight or nearly zero clearance.

9. The dental implant apparatus in accordance with claim 1, 2 or 3, further comprising a stop arranged on said instrument for limiting relative axial movement of said instrument with respect to the second sleeve after said connection has been released.

10. An apparatus comprising an instrument for preparing or executing insertion of a dental implant, a template configured to be placed on a bone or tissue surrounding the bone, said template or a first sleeve arranged in said template having a through-recess configured for passage therethrough of at least part of said instrument, an axially displaceable second sleeve that in a basic position is axially fixed on the instrument with pre-specified retention force by means of automatically releasable connecting elements and wherein when the retention force is exceeded said connecting elements are automatically releasable whereupon said second sleeve is axially displaceable on said instrument, and said instrument together with said axially fixed second sleeve being insertable into said through-recess and thereupon being guided and/or oriented in said template via the exterior surface of said second sleeve, said first sleeve being integrated into said template and the apparatus comprising stops arranged on said first sleeve and said second sleeve for securing said second sleeve against rotation with respect to said integrated first sleeve and said integrated first sleeve having a lateral slit configured to permit passage therethrough of at least a tip portion of said instrument so that said instrument or portion thereof can be inserted at an incline relative to and into the template and integrated first sleeve thereof to thereby enable agility in installation and handling of the instrument inside of an oral cavity.

11. A dental implant apparatus comprising an instrument for preparing or executing insertion of a dental implant, a template configured to be placed on a bone or tissue surrounding the bone, said template or a first sleeve arranged in said template having a through-recess configured for passage therethrough of at least part of said instrument, an axially displaceable second sleeve that in a basic position is axially fixed with pre-specified retention force by means of automatically releasable connecting elements, at least one of said releasable connecting elements being received within another of said releasable connecting elements, and wherein when the retention force is exceeded said connecting elements are automatically releasable whereupon said second sleeve is axially displaceable on said instrument, and said instrument together with said axially fixed second sleeve being insertable into said through-recess and thereupon being guided and/or oriented in said template via the exterior surface of said second sleeve, said releasable connecting elements comprising an elastic ring or expandable spring element partially received in an annular groove in the second sleeve and an annular groove on the exterior of the instrument in which the elastic ring or spring element is partially received.

12. The dental implant apparatus in accordance with claim 11, wherein said elastic ring or expandable spring is so configured as to retain said sliding sleeve on said instrument even after said connecting elements have been released.

13. The dental implant apparatus in accordance with claims 1 or 3, wherein said connecting elements are so configured that even after release thereof said second sleeve is retained on said instrument.

14. A dental implant apparatus comprising an instrument for preparing or executing insertion of a dental implant, a template configured to be placed on a bone or tissue surrounding the bone, said template or a first sleeve arranged in said template having a through-recess configured for passage therethrough of at least part of said instrument, an axially displaceable second sleeve that in a basic position is axially fixed on the instrument with pre-specified retention force by means of automatically releasable connecting elements, at least one of said releasable connecting elements being received within another of said releasable connecting elements, and wherein when the retention force is exceeded said connecting elements are automatically releasable whereupon said second sleeve is axially displaceable on said instrument, said instrument together with said axially fixed second sleeve being insertable into said through-recess and thereupon being guided and/or oriented in said template via the exterior surface of said second sleeve in which a tip of the instrument protrudes beyond a bottom surface of the second sleeve by a predetermined length that is substantially the same as a length of the second sleeve, an exterior surface of said instrument and an interior surface of said second sleeve are so dimensioned that the second sleeve is slidably fitted on the instrument with a slight or nearly zero clearance, said second sleeve has a contact surface positionable against said template and/or said first sleeve such that when the contact surface is urged against said template and/or said first sleeve the retention force is exceeded whereupon said connecting elements are automatically released, the basic position of the second sleeve is so predetermined that after the tip of said instrument has been at least partly inserted into said recess so that said guiding and orientation is effected, said automatic release occurs whereupon said second sleeve is slidable on the instrument, and said apparatus including stops on said second sleeve and said template or said first sleeve, said stops being located and configured to limit rotational movement of said second sleeve with respect to said template and/or said first sleeve, said connection between said second sleeve and said instrument being releasable when said limit has been attained and/or after a predetermined axial displacement of said second sleeve with respect to said template and/or said first sleeve due to application of an axial force.

* * * * *